US007183251B1

(12) United States Patent
Russo et al.

(10) Patent No.: US 7,183,251 B1
(45) Date of Patent: Feb. 27, 2007

(54) HCG THERAPY FOR THE TREATMENT OF BREAST CANCER

(75) Inventors: Irma H. Russo, Rydal, PA (US); Jose Russo, Rydal, PA (US); Giampiero Deluca, Geneva (CH); Jaak Janssens, Hasselt (BE)

(73) Assignees: Fox Chase Cancer Center, Philadelphia, PA (US); Applied Research Systems ARS Holdings N.V., Caraco (AN)

( * ) Notice: Subject to any disclaimer, the term of this patent is extended or adjusted under 35 U.S.C. 154(b) by 0 days.

(21) Appl. No.: 09/868,196

(22) PCT Filed: Dec. 15, 1999

(86) PCT No.: PCT/US99/29795

§ 371 (c)(1),
(2), (4) Date: Aug. 2, 2001

(87) PCT Pub. No.: WO00/35469

PCT Pub. Date: Jun. 22, 2000

(30) Foreign Application Priority Data

Dec. 15, 1998 (EP) .................................. 98123817

(51) Int. Cl.
*A61K 38/00* (2006.01)
(52) U.S. Cl. ......................................................... 514/2
(58) Field of Classification Search .................... 514/8, 514/2, 12
See application file for complete search history.

(56) References Cited

U.S. PATENT DOCUMENTS

| 5,677,275 A | 10/1997 | Lunardi-Iskandar et al. ... 514/8 |
| 5,700,781 A | 12/1997 | Harris ........................... 514/21 |
| 5,877,148 A | 3/1999 | Lunardi-Iskandar et al. ... 514/8 |

FOREIGN PATENT DOCUMENTS

| WO | WO 85/01959 | 5/1985 |
| WO | WO 96/04008 | 2/1996 |
| WO | WO 97/494432 | 12/1997 |

OTHER PUBLICATIONS

Grattarola (1976, Journal of the National Cancer Institute, vol. 56, pp. 11-16).*
Saal et al, Fertil Steril. Aug. 1991;56(2):225-9.*
Anapliotou et al, Fertil Steril. Aug. 1996;66(2):305-11.*
Silverstein et al (1994, Cancer, vol. 73, pp. 1673-1677, abstract only).*
Platanias et al (J Biol Chem. Mar. 6, 1998;273:5577-81).*
Oberg et al (1989, J Natl Cancer Inst., vol. 81, pp. 531-535).*
Recchia et al (Clin Ter. May-Jun. 1998;149:203-8).*
Sigma catalog (1995, p. 263 only).*
Robinson et al (1990, Breast Cancer Res. Treat., vol. 15, pp. 95-101, Sep. 4, 2003.*

Albini, et al., "The β-core fragment of human chorionic gonadotrophin inhibits growth of kaposi's sarcoma-derived cells and a new immortalized kaposi's sarcoma cell line", *Aids*, 1997, 11, 713-721.
Allegra, J.C. "Reviews on endocrine related cancer", Paterson AHG, Lees Aw eds Suppl, 1984, 14, 115-119.
Alvardo, et al., "Human chorionic gonadotropin inhibits proliferation and induces expression of inhibin in human breast epithelial cells in vitro", *In Vitro 30A*, 1994, 4-8.
Bernstein, et al., "Treatment with human chorionic gonadotropin and risk of breast cancer", *Cancer Epidemiol.*, Biomarkers and Prev. 1995, 4, 437-440.
Dias, J.A. et al., "Receptor binding and functional properties of chimeric human follitropin prepared by an exchange between a small hydrophilic intercysteine loop of human follitropin and human lutropin", *J. Biol. Chem.*, 1994, 269(41), 25289-25294.
Pouillart, P. et al., "Administration of fibroblast interferon to patients with advanced breast cancer: possible effects on skin metastasis and on hormone recepotrs", *Eur. J. Cancer Clin. Oncol.*, 1982, 18, 929-935.
Gill, et al., "Phase I study of human chorionic gonadotropin given subcutaneously to patients with acquired immunodeficiency syndrome-related mucocutaneous kaposi's sarcoma", *J. Natl Cancer Inst.*, 1997, 89, 1797-1802.
Grossman, M.et al., "Substitution of the seat-belt region of the thyroid-stimulating hormone(TSH) β-subunit with the corresponding regions of choriogonadotropin or follitropin confers luteotropic but not follitropic activity ti chimeric TSH", *J. Biol. Chem*, 1997, 272(24), 15532-15540.
Baulieu E.E. et al, Glycoprotein hormones: gonadotropins and thyrotropin. In Hormones-From molecules to Disease.Chapman and Hall, N.Y. and London, 1990, 257-275.
Legha, et al., "Antiestrogens in the treatment of breast cancer", *Cancer Treat. Rev.* 1976, 3, 205.
Lunardi-Iskandar, et al., "Effects of a urinary factor from women in early pregnancy on HIV-1, SIV and associated disease" *Nature Med*, 1998, 4, 428-434.
Mgbonyebi, et al., "Induction of reversible growth arrest of immortal and neoplastic human breast epithelial cells by human chorionic gonadotropin", *Proc. Annu. Meet. A, Soc. Cancer Res.*,1997, pp A1977, XP002109660.
Natoli, C. et al., "Two new estrogen-supersensitive variants of the MCF-7 human breast cancer cell line", *Breast Cancer Res Treat*, 1983, 3, 23-32.
Russo, et al., "Physiological bases of breast cancer prevention" *Euro J. Cancer Prevention*, 1993, 2, 101-111.

(Continued)

*Primary Examiner*—Misook Yu
(74) *Attorney, Agent, or Firm*—Drinker Biddle & Reath LLP; Janet E. Reed

(57) ABSTRACT

This invention relates to the field of cancer therapy. More particularly, the invention relates to the treatment of mammary tumor, clinically manifest mammary tumor (breast cancer) and metastatic mammary tumor by administration of human Chorionic Gonadotropin (hCG). The treatment preferably comprises the administration of hCG in conjunction with an antiestrogen and/or a Type I Interferon.

14 Claims, 8 Drawing Sheets

OTHER PUBLICATIONS

Russo, et al., "Is differentation the answer in breast cancer prevention?" *Inter. Res. Com*, 1982, 10, 935-945.

Russo, et al., "Susceptibility of the mammary gland to carcinogenesis", *Am J. Pathol*, 1979, 96, 721-734.

Russo, et al., "Developmental stage of the rat mammary gland as determinant of its susceptibility to 7, 12-Dimethylbenz[a]anthracene", *J. Natl. Cancer Inst.* 1978, 61, 1439-1442.

Russo, et al., Biology of Disease, "Biological and Molecular bases of Mammary Carcinogenesis", *Lab Invest*, 1987, 57, 112-137.

Russo, et al., "Human chorionic gonadotropin and rat mammary cancer prevention" *J. Natl. Cancer Inst.*, 1990, 82, 1286-1289.

Russo, et al., "Protective effect of chorionic gonadotropin on DMBA-induced mammary carcinogenesis", *Br. J. Cancer*, 1990, 62, 2343-2347.

Russo, et al., "Influence of differentation and cell kinetics on the susceptibility of the rat mammary gland to carcinogenesis", *Cancer Res.*, 1980, 40, 2677-2687.

Russo, et al., "Susceptibility of the mammary gland to carcinogenesis" *Am. J. Pathol*, 1980, 100, 497-511.

Samaneigo, F. et al., "Induction of programmed cell death in kaposi's sarcoma cells preparations of human chorionic gonadotropin" *J. Natl. Cancer Inst.*, 1999, 91, 135-143.

Srivastava, et al., "Chorionic gonadotropin inhibits rat mammary carcinogenesis through activation of programmed cell death", *Carcinogenesis*, 1997, 18, 1799-1808.

Srivastava, P. et al., "Growth inhibition and activation of apoptotic gene expression by human chorionic gonadotropin in human breast epithelial cells", *Anticancer Research*, 1998, 18, 4003-4010.

Srivastava, P. et al., "Identification of new genes differentially expressed in breast carcinoma cells treated with human chorionic gonadotropin", *Int'l Jrl of Oncology*, 1998, 13, 465-469.

You, et al., "direct modulation of tumor suppressor connexin 26 gene by human chorionic gonadotropin in rat mammary glands", *Cancer Research*, 1998, 58/7, 1498-1502.

* cited by examiner hCG CONCENTRATION (IU/ml)

HCG THERAPY FOR THE TREATMENT OF BREAST CANCER

This application claims priority to European Application No. 98123817.3, filed Dec. 15, 1998, the entirety of which is incorporated by reference herein.

FIELD OF THE INVENTION

This invention relates to the field of cancer therapy. More particularly, the invention relates to the prevention or treatment of clinically manifest mammary tumor (breast cancer) and metastatic mammary tumor by administration of human Chorionic Gonadotropin (hCG). The treatment of mammary tumor in postmenopausal women is also contemplated. The treatment preferably comprises the administration of hCG in conjunction with an antiestrogen and/or a Type I Interferon.

BACKGROUND OF THE INVENTION

Various patents and scientific articles are referred to throughout the specification. These publications are incorporated by reference herein to describe the state of the art to which this invention pertains.

Breast cancer has caused the death of a quarter of a million women worldwide for many years and has been estimated to be the leading cause of death in women aged between 35 to 54, being second only to cardiovascular diseases in women aged over 55 (W. P. D. Logan, Cancer of the female breast. International mortality trends. W. H. O. Stat. Rep. 28:232, 1975).

Breast cancer accounts for 27% of all malignancies around the world. Despite improvements in early detection of this disease, its incidence is increasing and its mortality rate has not significantly decreased. There is a well-known association between early full term pregnancy and a reduction in the lifetime risk of developing breast cancer, however the mechanisms mediating this protective effect have not been elucidated.

In the rat model, completion of a full term pregnancy prior to carcinogen administration inhibits tumor production. Maximal mammary tumor incidence occurs when the carcinogen is administered to young rats (Russo and Russo, 1987, Lab. Invest. 57:112–137; Russo and Russo, 1978, J. Natl. Cancer Inst. 61:1439–1442; Russo et al., 1979, Am. J. Pathol. 96:721–734). Tumor incidence decreases significantly, or becomes almost completely abolished when the carcinogen is administered to parous rats between 3 and 9 weeks post-delivery with or without lactation (Russo and Russo, 1980, Am. J. pathol. 100:497–511; Russo and Russo, 1980, Cancer Res. 40:2677–2687; Russo and Russo, 1982, Internat. Res. Com. (IRCS) 10:935–945; Russo and Russo, 1993, European J. Cancer Prevention 2:101–111).

The role played by endocrine treatment in breast cancer was discovered in 1896, when Bateson observed that breast cancer in pre-menopausal women undergoes remission after oophorectomy. This finding, subsequently confirmed by other scientists, supported the evidence that at least some breast tumors are directly dependent on hormones for their growth and created interest in the therapeutic approach of endocrine organ ablation for the purpose of removing the endogenous source of hormones.

As drugs specifically antagonizing the estrogen action were discovered, they became an attractive alternative to surgical ablation. Several anti-estrogen compounds have been tested in pre- and post-menopausal women in phase I and II clinical trials. So far, Tamoxifen has proved to be the drug best approaching the effectiveness of surgical endocrine therapy and the one that is substantially free from serious side effects. A comprehensive review of the therapeutic efficacy of antiestrogens in the treatment of breast cancer can be found in Legha & Carter, Antiestrogens in the treatment of breast cancer. (Cancer Treat. Rev. 3:205, 1976.). Another review more specifically related to clinical experience with Tamoxifen is that of Paterson et al, A review of the International clinical experience with Tamoxifen. (Jpn. J. Cancer Clin. 11 (Suppl.): 157, 1981).

Approximately one-third of women with breast cancer respond to antiestrogen-based hormonal therapy, while an increase up to 70% of response is expected in patients with receptor-rich tumors. In fact, estrogen receptor (ER) status has been demonstrated to be predictive of response in breast cancer patients (Allegra, J. C., Reviews on Endocrine related cancer. Paterson A H G, Lees A W eds Suppl. 14:115, 1984).

Chorionic gonadotropin is a glycoprotein hormone composed of two non-covalently linked ($\alpha$ and $\beta$) subunits. (Labrie, Glycoprotein hormones: gonadotropins and thyrotropin. In: Hormones—From Molecules to Disease. Beanlien E E and Kelly P A—Chapman and Hall, New York and London, pp 257–275, 1990). It is synthesized early in pregnancy by the developing embryo and throughout the gestational process by the syncytiotrophoblast of the placenta, and it is secreted in urine.

Human chorionic gonadotropin is obtained from the urine of pregnant women for both experimental and clinical uses. The hormone can also be prepared via the recombinant route (WO 85/01959) The main known function of hCG is the stimulation of gonadal steroid hormone production through its interaction with the LH/CG receptor, which is present in the granulosa cells of the ovary in the female and in the testicular Leydig cells in the male.

Recent studies have suggested that urinary hCG is a potent preventive agent that inhibits chemically-induced mammary tumorigenesis through the induction of differentiation. (Russo et al., J. Natl. Cancer Inst. 82:1286–1289, 1990). Additional experiments indicated that hCG treatment of rats after exposure to carcinogens also protected them from tumor development (Russo et al., Br. J. Cancer 62: 2343–2347, 1990). HCG also inhibits the proliferation of normal and neoplastic human breast epithelial cells (Alvarado et al., In Vitro 30A: 4–8, 1994). It has also been found that urinary hCG from various sources has an inhibitory effect on neoplastic cell lines from various organs or systems (Gill et al., J. Natl Cancer Inst. 89: 1797–1802, 1997; Albini et al., AIDS 11: 713–721, 1997; Mgbonyebi et al., Proc. Annu. Meet. A, Soc. Cancer Res. 38, PP. A1977, XP002109660, 1997).

International Patent Application WO 97/49432 describes the induction of cell death of breast cancer cells in vitro by treatment of the cells with urinary hCG. The same effect was observed with various fractions and the hCG $\beta$-subunit.

Two further studies, both performed in a rat model, showed that urinary hCG has a preventive effect against carcinogen-induced rat mammary tumors (Srivastava et al., Carcinogenesis 18: 1799–1808, 1997 and You et al., Cancer Research 58/7: 1498–1502, 1998). Rats were pre-treated with daily doses of urinary hCG for several weeks before tumor induction and sacrificed at various time points after continued hCG treatment. In the pre-treated rats, the incidence of carcinoma-induced mammary tumors was reduced.

Women who had undergone urinary hCG treatment for infertility or weight loss also were observed to have a reduced incidence of breast cancer (Bernstein et al., Cancer Epidemiol., Biomarkers and Prev. 4: 437–440, 1995). These observations were only inferential, however, and studies directed toward measuring the effect of hCG in the treatment of human breast cancer heretofore have not been reported. From the rat model, only a protective effect of urinary hCG on the development of cancer has been deduced when the hCG was administered very close to initiation of carcinogenesis. However, in humans, breast cancer is usually diagnosed only after it is already established as a palpable nodule, or detectable in diagnostic mammography.

U.S. Pat. No. 5,700,781 (Harris, 1997), U.S. Pat. Nos. 5,677,275 and 5,877,148 (Lunardi-Iskandar et al., 1997, 1999), as well as International Patent Application WO96/04008 disclose methods for treating cancers like Kaposi's sarcoma, involving the administration of urinary hCG. For Kaposi's sarcoma, which is believed to be of endothelial origin, the hCG seemed to have an anti-proliferative effect when injected into mice having established, metastatic Kaposi's sarcoma.

Recently, the anti-tumor effects of hCG were questioned by a series of experiments reported by the group of Robert Gallo (Lunardi-Iskandar et al., Nature Med. 4: 428–434, 1998 and comments at pages 370 and 390–391 of the same issue). These experiments convincingly showed that the anti-Kaposi's Sarcoma (KS) effect of hCG preparations are not due to the hCG itself, but instead to an unidentified urinary factor, referred to as HAF (hCG-associated factor). A number of commercially available hCG preparations (clinical grade and purified), as well as subunits, fragments and recombinant hCG, were tested for their inhibitory activity on neoplastic KS cells in vitro and in in vivo animal models. Neither purified urinary nor purified recombinant hCG, subunits or fractions of hCG had any effect in the in vivo animal model or in vitro assay, respectively.

The fact that early pregnancy of mice leads to KS tumor regression even though mice do not produce hCG at all further supports these findings.

Taken together, evidence accumulated that the beneficial effects of hCG in treating cancer were just an artifact of insufficient protein purification, the actual anti-tumor agent being an as-yet unidentified factor associated with early pregnancy. The results obtained with recombinant hCG, together with the fact that the source of the hCG-associated factor "HAF" was first-trimester pregnancy human urine, ruled out the possibility of obtaining any anti-tumor activity from recombinant hCG preparations.

SUMMARY OF THE INVENTION

The inventors of the present invention have now made the surprising discovery that both urinary as well as recombinant hCG is effective in the treatment of human breast cancer. This finding overcomes the prejudice created within the scientific community by the experiments of Gallo et al., outlined above (Lunardi-Iskandar et al., supra), wherein the anti-tumor activity was not traced back to hCG.

The present invention therefore relates to the use of hCG for the manufacture of a medicament for the prevention of mammary tumors, and to corresponding pharmaceutical compositions, methods of treating patients with those pharmaceutical compositions, and articles of manufacture comprising such pharmaceutical compositions.

In addition, the inventors have found that hCG is effective in the treatment of conclamate human mammary tumors, i.e., mammary tumors that are already clinically manifest.

The present invention also relates to the use of hCG for the manufacture of a medicament for the treatment of clinically manifest or evident mammary tumors, and to corresponding pharmaceutical compositions, methods of treating patients with those pharmaceutical compositions, and articles of manufacture comprising such pharmaceutical compositions.

Other features and advantages of the present invention will be better understood by reference to the drawings, detailed description and examples that follow.

DETAILED DESCRIPTION OF THE INVENTION

Figure 1:
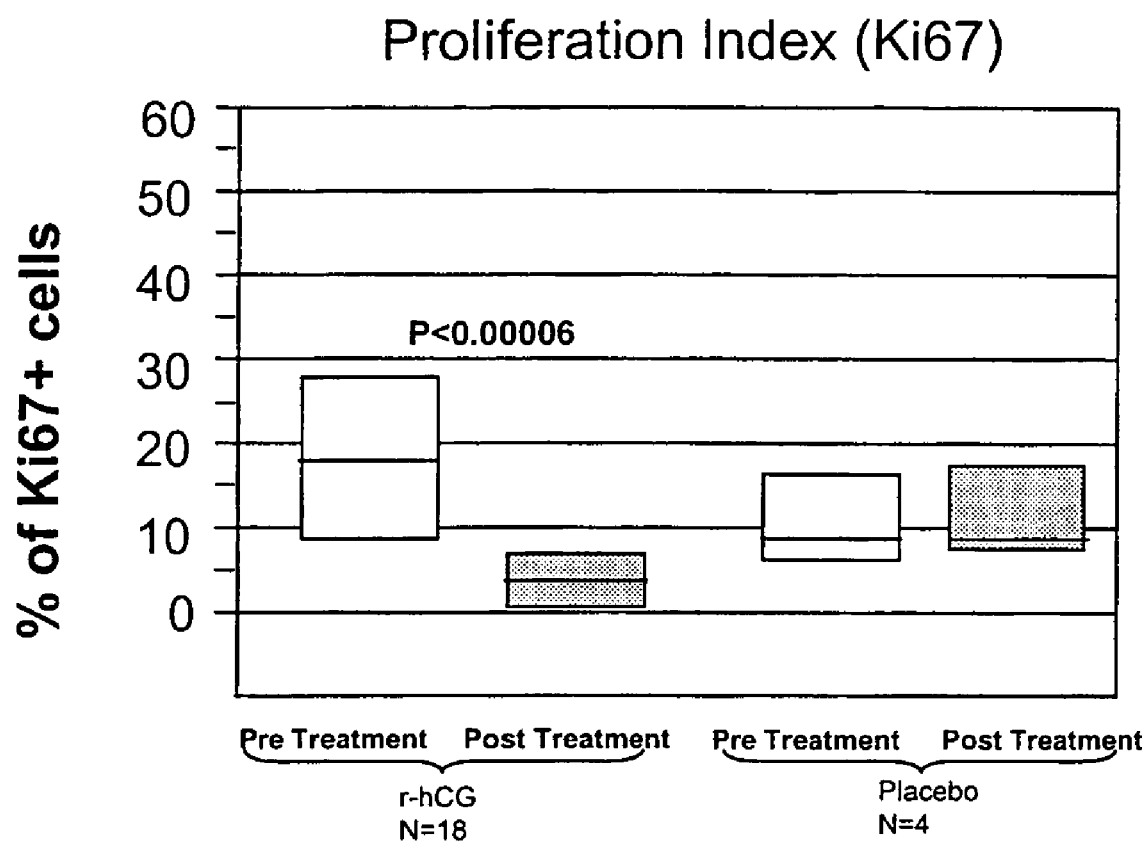
FIG. 1. Histogram showing the effect of r-hCG treatment on the proliferative index of primary human breast cancers (ki67+ cells). Women with clinically apparent, newly diagnosed cancer of the breast underwent pre-treatment needle biopsies of the breast mass. They then received either every other day injections of 500 mcg r-hCG, or no treatment. The breast mass was then removed by lumpectomy or mastectomy. The proliferative index of the needle biopsies and excised tumors were determined by immunohistochemical staining for Ki67+ cells.

In accordance with the present invention, it has now been shown that hCG is effective in the prevention of mammary tumors and in the treatment of conclamate human mammary tumors, i.e. of mammary tumors, which are already clinically manifest. The invention therefore relates to the use of hCG for the manufacture of a medicament for the prevention of mammary tumors and for the treatment of clinically manifest or evident mammary tumors.

Clinically manifest is to be understood as being detectable using clinical diagnostic methods, as palpation, mammography, ultrasound or other imaging diagnostics as thermography, light scanning, xeroradiography or Magnetic Resonance Imaging (MRI), scintigraphy and so on, but also the diagnostic detection from histological examination of biopsy material, as for example fine-needle aspiration biopsy, or form serological markers.

In a preferred embodiment, the clinically manifest tumor is a primary tumor, meaning that the tumor has not been disseminated and infiltrated other tissues, but is still at the primary site where it developed. Preferably, the primary tumor is a non-invasive carcinoma, such as ductal carcinoma in situ, derived from the epithelium of the mammary gland duct, or lobular carcinoma in situ, derived from the secretory epithelium of the mammary gland.

In another embodiment, the tumor is an invasive carcinoma, which can be invasive tubular or lobular (glandular) carcinoma or any other invasive or infiltrating breast cancer. The tumors treated according to the invention can also be of other histological types, such as medullary, mucinous, papillary and the like.

Breast cancer exists in women and in men. However, it is highly prevalent in women. Breast cancer can occur in premenopausal or postmenopausal women. The invention therefore also relates to the use of hCG for the manufacture of a medicament for the treatment and/or prevention of mammary tumors in premenopausal or postmenopausal women, though it may be used to treat breast cancer in men as well.

As can be taken from the clinical studies on postmenopausal women presented in Example 2 below, the women treated had bi-dimensionally measurable or palpable lesions and clinical evidence of metastatic disease, and hCG had a positive effect on the course of the illness in more than 50% of the patients. The invention therefore preferably relates to the treatment of mammary tumors in postmenopausal women. The invention also relates to the use of hCG for the manufacture of a medicament for the treatment and/or prevention of metastatic mammary tumors. Highly preferred is the use of hCG for the preparation of a medicament for treatment of metastatic mammary carcinoma in postmenopausal women.

In another preferred embodiment, hCG is used as an adjuvant in combination with other cancer therapies. Other cancer therapies include, for example, mastectomy, lumpectomy, segmental mastectomy or any other surgical treatment, as well as chemotherapy, or therapy with drugs or combinations of drugs.

For instance, specific endocrine therapies with antiestrogens, progestins or aromatase inhibitors have been found to be effective in treating breast cancer. Antiestrogens are especially effective in the treatment of Estrogen-receptor (ER) positive tumors, since they bind to the ER and competitively block binding of estrogen to its receptor. The invention therefore also relates to the treatment or prevention of breast cancer wherein the treated tumor cells are Estrogen-Receptor positive, and to the use of hCG in combination with an antiestrogen. The administration of hCG and the antiestrogen may be simultaneous, sequential or separate.

The administration of the antiestrogen sequentially to the treatment with hCG is particularly preferred. The antiestrogen particularly well suited is Tamoxifen, which may be administered orally in a daily amount of about 30 milligrams (mg). Although Tamoxifen is the preferred antiestrogen, other substances having analogous activity are within the meaning of "antiestrogen" in accordance with the present invention. Suitable examples are found, e.g., in a review by Legha and Carter: "Antiestrogens in the treatment of breast cancer" (Cancer Treat. Rev. 3:205, 1976).

The amount of hCG administered according to the invention is 100 to 20,000 International Units (IU) per day or equivalent microgram (µg) amounts. The unit "IU" is specifically adapted to biologically active substances. The International Unit "IU" of hCG is the activity contained in a stated amount of the International Standard, which consists of a mixture of freeze-dried extract of chorionic gonadotrophin from the urine of pregnant women, with lactose. The equivalence in the International Units of the International Standard is stated by the World Health Organization. The potency of hCG is expressed in International Units per milligram. The determination of the potency is described in European Pharmacopoeia 1997, pp. 913–914 or in USP, *Gold/Official Monographs*, p. 718. The protein content of a preparation can be measured by any protein determination assay known in the art, as for example by the Lowry protein assay or Bradford protein assay, based on measuring optical density, as well known by persons skilled in the art.

Commercial urinary hCG preparations have a specific activity range of 2,000 to 10,000 IU/mg, for example. Recombinant hCG preparations may have a specific activity as high as 20,000 IU/mg. Daily doses in the range of 5,000 to 10,000 IU/day/patient are preferred. Using mass to calculate dosage, hCG may be administered in an amount of 50 to 10,000 micrograms per patient per day. An amount of 250 to 3,000 micrograms per patient per day is preferred. Preferably, hCG administered every second day, or three times a week.

The duration of hCG administration preferably is several weeks. In particular, the administration of hCG every two days lasts for about 12 weeks. A highly preferred regimen is an administration every two days for about 12 weeks, a regimen that is particularly applicable to the treatment of metastatic breast cancer in post-menopausal women.

The hCG may be administered locally, i.e. directly into or onto the tumor, or it can be administered into the blood stream. It can also be administered intramuscularly. In a preferred embodiment the administration is subcutaneous.

The present invention also provides pharmaceutical compositions containing a pharmaceutically active amount of an hCG and an antiestrogen, in the presence of one or more pharmaceutically acceptable excipients, for the simultaneous, sequential or separate use of its active components in the treatment of breast cancer.

Suitable pharmaceutically acceptable excipients include any and all solvents, dispersion media and the like which may be appropriate for the desired route of administration of the pharmaceutical preparation. The use of such excipients for pharmaceutically active substances is known in the art. Except insofar as any conventional media or agent is incompatible with the compositions to be administered, its use in the pharmaceutical composition is contemplated. In preferred embodiments, the pharmaceutical compositions contain hCG or a biological equivalent thereof (preferably 250–500 µg hCG) and a sugar (preferably 30–60 mg sucrose) in a phosphate buffer. The preparation preferably is lyophilized for storage and transportation, then re-constituted with water or saline before use.

The pharmaceutical compositions according to the invention is administered in an amount of 100 to 20,000 IU or equivalent mass amounts calculated from the specific activity (preferably about 500 μg, equivalent to about 10,000 IU), preferably to be administered subcutaneously. The antiestrogen preferred for use in the pharmaceutical compositions of the invention is Tamoxifen, which is administered orally in a daily amount of about 30 milligrams.

Interferons (IFNs) are a well-known family of proteins which have been shown to possess both antiviral and cell growth inhibitory effects. Therefore, a preferred embodiment of the invention makes use of an interferon, preferably a Type I Interferon in the treatment of breast cancer in combination with hCG and an antiestrogen. This combination further reduces the growth of breast cancer cells. The term "Type I Interferon" is intended to include IFN-α (alpha), IFN-β (beta), IFN-ω (omega) or IFN-τ.

Interferons have a wide range of cellular effects on cancer cells, as well as on normal cells, including effects on cell phenotype such as expression of surface antigens and receptors, among others. Experimental evidence indicates that type I IFN modifies the hormone receptor level in breast cancer cells. For instance, Pouillart et al., in "Administration of fibroblast interferon to patients with advanced breast cancer: possible effects on skin metastasis and on hormone receptors" (Eur. J. Caner Clin. Oncol. 18:929–935, 1982) described the effect of human fibroblast interferon administered to patients with metastasized breast cancer and found an increase of the receptors for estrogens and progestins. It is for these reasons that the present invention includes the use of hCG and Type I Interferon in conjunction with an antiestrogen in the manufacture of a medicament for the treatment of breast cancer as well as a pharmaceutical composition therefor, for the simultaneous, separate or sequential use of its active components in the treatment of breast cancer.

Several forms of hCG may be used effectively in accordance with the present invention. These include the full dimer hCG and any fragment thereof having the similar biological activity of hCG and/or binding activity to the hCG receptor. hCG can be either "native", that is, obtained from natural human sources (urine, for example) or cell lines, or "recombinant", that is, obtained from genetically engineered or otherwise modified bacterial, yeast or eukaryotic cells.

It is well understood that the cellular receptor to which hCG binds also is recognized and bound by luteinizing hormone (LH), a hormone that is also structurally similar to hCG. For this reason, the present invention also includes the use of LH as a substitute for or supplement to hCG in any of the medicaments, pharmaceutical preparations and methods described herein. The appropriate dosage and regimen for administration of LH will be proportionate to that of hCG, wherein, as a rule of thumb, 1 IU of hCG is equivalent to 7 IU of LH.

In view of the common structure between the alpha subunits of FSH (follicle stimulating hormone), TSH (thyroid stimulating hormone), LH and hCG, the present invention is also directed to the use of FSH, TSH and LH fusion proteins, wherein the beta subunit has been modified so that the resulting fusion molecule has hCG-like behavior. Fusion molecules as contemplated herein are described in the art, e.g., by Dias et al., J. Biol. Chem. 269(41): 25289–25294 (1994); and Grossman et al., J. Biol. Chem. 272(24): 15532–15540 (1997).

The present invention also provides a method of inhibiting the proliferation of breast cancer cells in humans, preferably women, most preferably postmenopausal women, comprising administering to a patient in need thereof an effective inhibiting amount of hCG. Additionally, the invention provides a method of inhibiting the proliferation of metastatic mammary tumor cells, comprising administering an effective inhibiting amount of hCG.

The invention further relates to a method of inhibiting the proliferation of metastatic mammary tumor cells in humans, preferably women, most preferably postmenopausal women, comprising administering to a patient in need thereof an effective inhibiting amount of hCG. In a preferred embodiment, the aforementioned methods comprise additionally administering an effective inhibiting amount of an antiestrogen. In a particularly preferred embodiment, the methods comprise additionally administering a Type I Interferon.

The above-described aspects of the present invention relate to the treatment of clinically manifest mammary tumors. It is important to recognize that the experiments that led to these aspects of the invention also demonstrated unequivocally, for the first time, that hCG is efficacious as a prophylactic agent in protecting against mammary tumor development, and as a therapeutic agent in the treatment of existing tumors. This result was surprising in view of the recent reports that hCG was not effective in the treatment of AIDS related Kaposi's sarcomas, thus indicating that the alleged active principle (if any) in urinary hCG preparations is not hCG itself. It is particularly surprising that pre-existing breast carcinomas can be treated with hCG, and more specifically with r-hCG, inasmuch as programmed cell death is implicated as the mode of action of urinary hCG in both Kaposi's Sarcoma and breast cancer, and the aforementioned reports attributed the apoptosis activity of urinary hCG preparations to hCG-associated factors (HAFs) and not to hCG itself (Lundardi-Iskandar et al., Nature Medicine 4:428–434, 1998; Samaneigo et al., J. Natl. Cancer Inst. 91:135–143, 1999).

In view of the foregoing unexpected results, the present invention also relates to the use of hCG and particularly r-hCG for the manufacture of a medicament for the prevention of mammary tumors. Also provided are pharmaceutical compositions for the prevention of mammary tumors, which comprise r-hCG alone or in combination with one or more additional prophylactic or therapeutic agents, similar to the pharmaceutical compositions described above for the treatment of clinically manifest mammary tumors. Likewise, a method of preventing mammary tumors is provided, which comprises administering to a patient a prophylactically effective dose of r-hCG, for a duration effective to achieve a protective effect against mammary tumor development.

The dosage of hCG, the dosage regimen and the duration of the treatment for prevention of mammary tumors should be similar to those used for the treatment of clinically manifest tumors. Thus, in a preferred embodiment, the dosage of hCG for a human patient is from 100 IU to 50,000 IU (International Unit) per dosage, and in a more preferred embodiment, 1,000 to 20,000 IU. In a most preferred embodiment, the dosage is 10,000 IU. The dosage regiment may be from once a week to seven times a week, but preferably is on alternate days or three times a week. In another preferred embodiment, the dosage regimen is three times a week. The duration of administration of r-hCG preferably is several weeks, and most preferably about 12 weeks.

The use of hCG as a breast cancer preventative is appropriate for a variety of patients. For instance, patients with a family history of breast cancer stand to benefit greatly from this prophylactic measure. Similarly, patients with a personal or family history of other kinds of cancer, particularly hormone related cancer, would be likely candidates for preventative hCG treatment. The treatment preferably is administered to persons who have not undergone full-term pregnancy.

Articles of manufacture are also provided in accordance with the invention, to facilitate the use of hCG (including u-hCG, r-hCG, hCG β-subunit or any other hCG fragment or derivative having anti-cancer activity), hLH or fusion proteins comprising hCG β-subunit and corresponding subunits of FSH, TSH or LH, in a medicament, or as part of a pharmaceutical composition, in the above described methods for preventing mammary tumors or treating clinically manifest mammary tumors. Such articles of manufacture include packaging material, an hCG pharmaceutical composition within the packaging material, and a label that indicates that the pharmaceutical agent contained therein is useful for the prevention or treatment of mammary tumors.

The following examples are provided to describe the invention in greater detail. They are intended to illustrate, not to limit, the invention.

EXAMPLE 1

Recombinant Human Chorionic Gonadotrophin Inhibits Primary Mammary Tumor Growth in Postmenopausal Women The efficacy of hCG was evaluated by treating with this hormone patients with newly diagnosed primary breast cancer. The efficacy of treatment was assessed by determining whether administration of 10,000 IU hCG on alternate days for 2 weeks to women with newly diagnosed breast cancer will reduce tumor size, inhibit cell proliferation, and modify the percentage of cells expressing estrogen and progesterone receptors. The systemic effect of the hormone was evaluated by determining serum levels of pituitary and ovarian hormones at various times of treatment. R-hCG was used in this study.

Patient Selection and Accrual. Twenty-five postmenopausal women took part in the study. The patients had palpable and bidemensionally measurable primary breast cancer larger than 1.5 cm in clinical diameter. The tumor was confirmed by histopathological analysis. No evidence of metastatic disease was observed when entering the study. Patients had adequate bone marrow, hepatic and renal function. Patients with ulcerated tumors, skin involvement of inflammatory breast cancer were excluded. No concomitant pituitary nor ovarian tumors were observed among the patients. There was no active thrombophlebitis or a history of allergy to hCG. None of the patients had hormonal replacement therapy. A routine staging procedure consisted of cytological evaluation of a needle punction of the suspected lesion, medical history, thorough physical and gynecological examination, chest radiograph, sonography of the liver, abdomen and pelvis, bone scintigraphy, blood examination—including CA 15.3 tumor marker, mammography and sonography of the breasts. The primary tumor was measured by clinical examination, mammography and sonography immediately before surgery.

Specimen Collection and Post-Surgical Treatment. After informed consent, the patient underwent core biopsies of the primary tumor under local anesthesia with a pistol fitted with a 12 to 14 gauge tru-cut type biopsy needles (Bard, Covington, USA). This procedure represents the standard of care, therefore no departure from routine diagnostic procedures was required. The core needle biopsy was examined by frozen section technique. If the frozen section was positive for malignancy, then three additional needle biopsies were obtained from the tumor for evaluating the surrogate markers listed below. On the same day 0 (pretreatment) a serum sample was taken for determination of basal levels of inhibin, estrogen, progesterone, FSH, LH and the beta subunit of hCG. The serum sample, as was the case for all subsequent sera, was derived from the blood sample and frozen immediately at −70° C. until the day of shipment to the research laboratory. The other serum samples were obtained at days 5, 9 and 13. At day 15 of hCG treatment the patient underwent surgery, which consisted of mastectomy when the tumoral mass (including 'in situ' components) was considered to be larger than 3 cm; otherwise the breast was conserved and a lumpectomy was performed. Breast conservation was only practiced when the surgical margins were free of disease. Lymph node dissection of the axilla was routineously performed. All resected tissues was sent to the laboratory of pathology for microscopical examination.

After surgery the patients underwent adjuvant treatment. It consisted of 20 mg per day Tamoxifen when the tumor was larger than 3 cm or pathological lymph nodes were present. Hormonal adjuvant therapies are normally continued for 5 years. Post-surgical radiation was performed in those cases in which the breast was preserved, when the margins of resection on the chest wall were positive, or when the tumors were medially located. The breast was irradiated up to 50 Gray in 25 fractions of 2 Gray. The site of the primary tumor was boosted up to 66 Gray. The subclavicular lymph nodes and chest wall received a dose of 46 Gray in 23 fractions of 2 Gray. Each week 5 fractions were delivered. After primary treatment the patient was seen every three months for clinical examination and blood chemistry. Yearly, a radiological control was performed as well. In case of recurrent disease, treatment for recurrent breast cancer was initiated.

Hormonal Treatment: Dose and Schedule. The patients selected for this study received intramuscularly (IM) 10,000 units of the experimental drug, recombinant human chorionic gonadotropin on days 1, 3, 5, 7, 9, 11 and 13. The lyophilysate was reconstituted with normal physiological saline immediately before injection in the gluteus. The controls were blinded and received IM injections of placebo. At each injection the patients were seen and informed about there concurrent medication and possible side effects. Treatment was double blind with 20 active sets and 5 controls. No dose modification was allowed. When side effects occurred or concomitant clinical problems, the treatment was interrupted as was the case in one patient. The efficacy of treatment was assessed by evaluating in the residual tumor resected by lumpectomy or mastectomy at the end of the two-week r-hCG treatment the same parameters evaluated in the initial core needle biopsies.

Surrogate Marker Analysis. The effects of r-hCG on the breast tumors was evaluated by using immunocytochemistry, performed in both core biopsies of the tumor and in residual tumor present in lumpectomy or mastectomy specimens. The following surrogate markers were evaluated using immunocytochemistry: Rate of cell proliferation, percentage of cells positive for estrogen (ER) and progesterone receptors (PgR) and immunoreactivity for inhibin. The microscopic analysis of these surrogate markers were performed by selecting fragments of tumor as distant as possible from the sites in which needle biopsies had been performed in order to avoid confounding effects induced by healing and inflammation. The study of lymph nodes of the same patients from which the primary tumors were studies was also analyzed by the same techniques.

Breast Tumor Tissue Processing. One core biopsy of the breast tumor was performed in each patient selected for this protocol. The core biopsy was frozen and histologically analyzed by the pathologist. If the diagnosis of invasive carcinoma was made, three additional cores of tumor tissues were obtained at the time of the initial diagnosis. The cores were fixed in 10% neutral buffered formalin (NBF) for their histopathological and immunocytochemical analysis. The surgical specimens containing the tumor, i.e., lumpectomies or mastectomies, were fixed in NBF and representative fragments of the residual tumor and normal breast tissue distal to the tumor were sent to the clinical laboratory. Lymph nodes that were found to be positive for metastasis during axillary dissection were fixed in NBF, embedded in paraffin, and representative tissue blocks were also submitted. Every specimen was identified with the patient trial number, date in which the specimen was obtained, and whether it was the initial needle biopsy of tumor or of normal tissue, or the final (second) operative specimen consisting of either tumor or normal tissue. Formalin-fixed needle biopsy and tumor specimens were shipped to the clinical laboratory by express mail. All specimens were identified upon arrival to the laboratory by experiment number (Exp. 721) and an accession number which was sequentially assigned by date of arrival. All samples were identified at all times by their accession number; patient identity and treatment were disclosed only after all the data had been collected.

Immunocytochemical Studies

Antibodies. Cell proliferation—Ki67 monoclonal antibody (oncogene Science, Inc., Cambridge, Mass.); estrogen receptor—mouse monoclonal anti-human estrogen receptor antibody (ER) (clone ER1D5) (Amac Lab, Westbrook, Me.) diluted 1:400; Progesterone receptor (PgR)—mouse monoclonal antibody clone PR10A9 (Immunotech, Inc., Westbrook, Me.); rabbit polyclonal antibodies raised against inhibin a and b synthetic peptides synthesized at the laboratory's Protein synthesis Facility were used at a dilution 1:50.

Procedures. Sections of paraffin-embedded tissues were mounted on aminoalkylsilane-coated slides, deparaffinized, rehydrated and endogenous peroxidase was quenched with 2% hydrogen peroxide. After blocking, the sections were incubated with the respective antibodies overnight, washed and incubated with horse anti-mouse biotinylated secondary antibody (Vector Laboratories, Inc., Burlingame, Calif.). Vectastain Elite ABC kit (Vector Laboratories, Inc., Burlingame, Calif.) was used to conjugate and 3,3'-diaminobenzidine-HCl (DAB) to reveal the immunocytochemically reacted sites. Sections incubated with non-immune serum were used as negative controls. All sections were lightly counterstained with hematoxylin. Cell proliferation was evaluated by counting the number of cells expressing the nuclear antigen Ki67 in the outer part of the nucleolus and in the granular component of the nucleus. The possibility that intrapersonal variations might be affecting the results were ruled out by evaluating the same specimens several times blindly. Steroid receptor status was evaluated in serial sections reacted with the ER or PgR antibodies by a count of the number of nuclei positive for each one of the receptors. Values were expressed as the percentage of positive cells over the total number of tumor cells present in each tissue section. Immunostaining for inhibin was evaluated by examination of slides under a bright field microscope, and graded according to the intensity of the brown staining as negative (−), weakly (+), moderately (++) or strongly (+++) positive. Comparisons were made between values obtained in the first biopsy and in the tissues resected after 2 weeks of hCG treatment.

Apoptosis was detected in 5 mm sections of formalin-fixed, paraffin embedded tissues obtained as described above. Apoptotic cell nuclei were identified using the Apoptag kit (Oncor, Gaithersburg, Md.). Sections were first treated with 20 mg/ml proteinase K in PBS for 20 min. at room temperature, quenched by 0.002% $H_2O_2$ for 30 minutes, equilibrated with buffer, and incubated with terminal deoxynucleotidyl transferase (TdT) for 20–40 min. all procedures performed at room temperature. The sections were then washed with stop buffer for 30 min at 37° C., and incubated with anti-digoxigenin for 30 min at room temperature. Color was developed using 0.05% 3-3-dimethylaminobenzene in 0.01% $H_2O$ diluted with Tris-HCL (pH 7.5) and counterstained with Hematoxylin. The percentage of positive cells over the total number of cells counted represented the Apoptotic Index.

The evaluation of all the immunocytochemical reactions was done blindly by one of the Principal Investigators (JR), without knowledge of the type of treatment received by the patients. Only after all the data were collected and analyzed patient identity and the type of treatment were disclosed with the purpose of tabulating the data.

Evaluation of Systemic Effects of R-HCG

The systemic effects of this hormonal treatment was evaluated by determining serum levels of the pituitary hormones FSH and LH, and the ovarian hormones estrogen, progesterone, and inhibin as markers of hCG activity. Ten ml of blood were drawn on days 0, 5, 9 and 13 of treatment, from 26 patients. The serum was separated immediately upon drawing, frozen at −80° C. and the specimens were identified with the patient trial number, date, and sequence in the number in the treatment. The sera were shipped from Belgium to the clinical laboratory in dry ice by express mail. All specimens were identified upon arrival at the laboratory by experiment number and an accession number which was sequentially assigned by date of arrival.

Frozen serum samples were shipped to InterScience Institute (ISI), Inglewood, Calif., for radio immunoassay (RIA) quantitative determination of levels of the following hormones: hCG beta subunit, estradiol, progesterone, FSH; LH; and inhibin. Quantitative determination of beta-hCG was confirmed by SmithKline—Beechman Clinical Laboratories in Philadelphia, Pa.

Results

From the twenty five patients entered in this study the histopathological and immunocytochemical analysis could be completed in 22 of the patients. Tissues from three patients were not adequate for analysis because the amount of tumor was either insufficient or not properly preserved for immunocytochemical determination of cell proliferation, steroid receptors or inhibin.

Cell proliferation. The immunocytochemical detection of Ki67 revealed that at the initiation of treatment there was a significant variation in the rate of cell proliferation among the patients, as shown in the needle biopsy (NB) data. The tumors removed after the r-hCG treatment had significantly depressed values, with small interpersonal variations, whereas in those patients receiving the placebo the tumors had a cell proliferation rate almost identical to the initial values. The reduction in cell proliferation was significant ($p<0.00006$) (FIG. 1) in 17 out the 18 patients that received r-hCG treatment. In nine patients treated with r-hCG lymph nodes found to be positive at the time of surgery were available for analysis. In these nodes the metastatic cells had a rate of cell proliferation within the same range than the primary tumor removed at surgery, and significantly lower than in the needle biopsy. Positive lymph nodes in a placebo treated patient exhibited the same rate of cell proliferation than the NB and Exc.B. The carcinoma cells metastatic to the lymph nodes had a markedly lower rate of cell proliferation than the germinal centers, which contained numerous Ki67 positive cells.

In order to determine whether the effect of r-hCG treatment on cell proliferation was not masked or altered by the local trauma caused by the core biopsy, we have performed pilot experiments for validating the use of breast core biopsies for determining surrogate end points of cell proliferation in collaboration with Dr. Ingemar Persson, from the Department of Cancer Epidemiology, Uppsala University, Uppsala, Sweden. A pilot study was designed with the purpose of validating data on normal breast morphology and cell proliferation observed in breast core biopsies obtained utilizing a pistol fitted with a 18 gauge needle by their comparison with the same parameters measured in large specimen samples obtained by reduction mammoplasty. Core biopsies were performed in four patients. Each biopsy measured approximately 2 cm in length by 0.2 cm in diameter. The material was fixed in buffered formalin, embedding in paraffin, and stained with hematoxylin and eosin and reacted against Ki67, a proliferating marker. We found the same lobular structures present in the core biopsy were also observed in the surgical specimen. The proliferating activity was not statistically different in the cells from the core biopsy than in those from the reduction mammoplasty specimens (unpublished observations). These data were confirmed in the present study in which the values of cell proliferation detected in the mastectomy specimen were similar to those detected in the dissected lymph nodes. Altogether, these preliminary data allowed us to rule out the possibility that the effect of r-hCG might have been induced by the local manipulation and not by the administered hormone.

Figure 2:
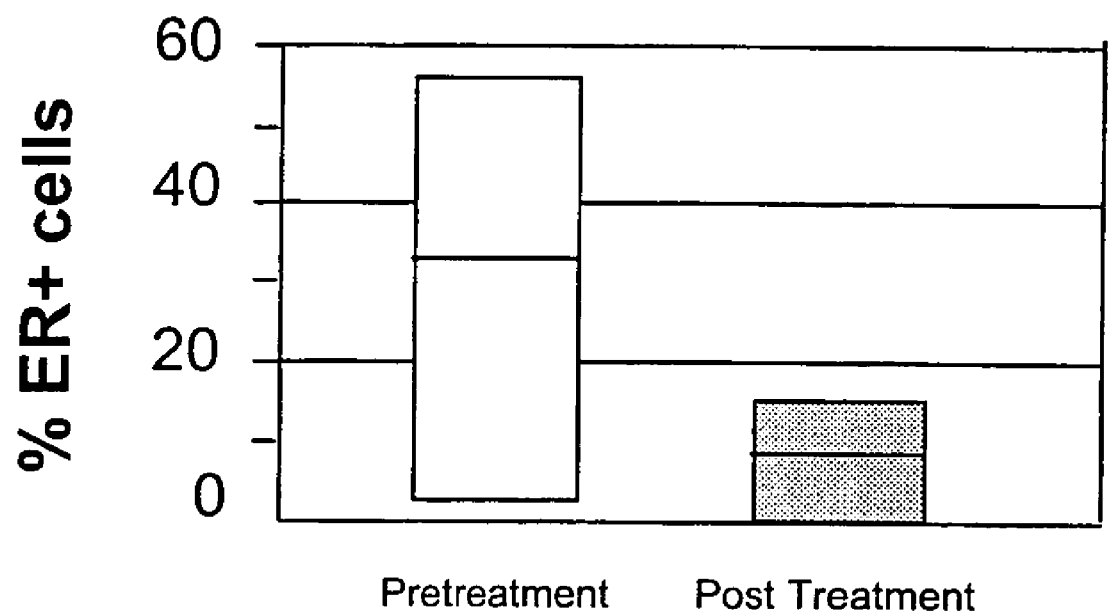
FIG. 2. Histogram showing the effect of r-hCG treatment on the estrogen receptor expression of primary human breast cancers (Er+ cells). Women with clinically apparent, newly diagnosed cancer of the breast underwent pre-treatment needle biopsies of the breast mass. They then received either every other day injections of 500 mcg r-hCG, or no treatment. The breast mass was then removed by lumpectomy or mastectomy. The estrogen receptor expression of tumor cells in the needle biopsies and excised tumors were determined by immunohistochemical staining for Er+ cells.

Estrogen and progesterone receptor. The immunocytochemical expression of ER was considered to be positive when greater that 20% of tumoral cells expressed a positive nuclear reaction for this receptor. Based upon this concept, it was found that in six cases r-hCG treatment resulted in a decrease in the ER status from a positive NB to a negative Exc.B (FIG. 2). The lymph node metastases of these patients showed a similar level of ER, except in two cases that expressed an ER content similar to that of the initial biopsy. None of the placebo treated groups showed changes in their receptor content between the initial biopsy and the post-treatment specimen.

Figure 3:
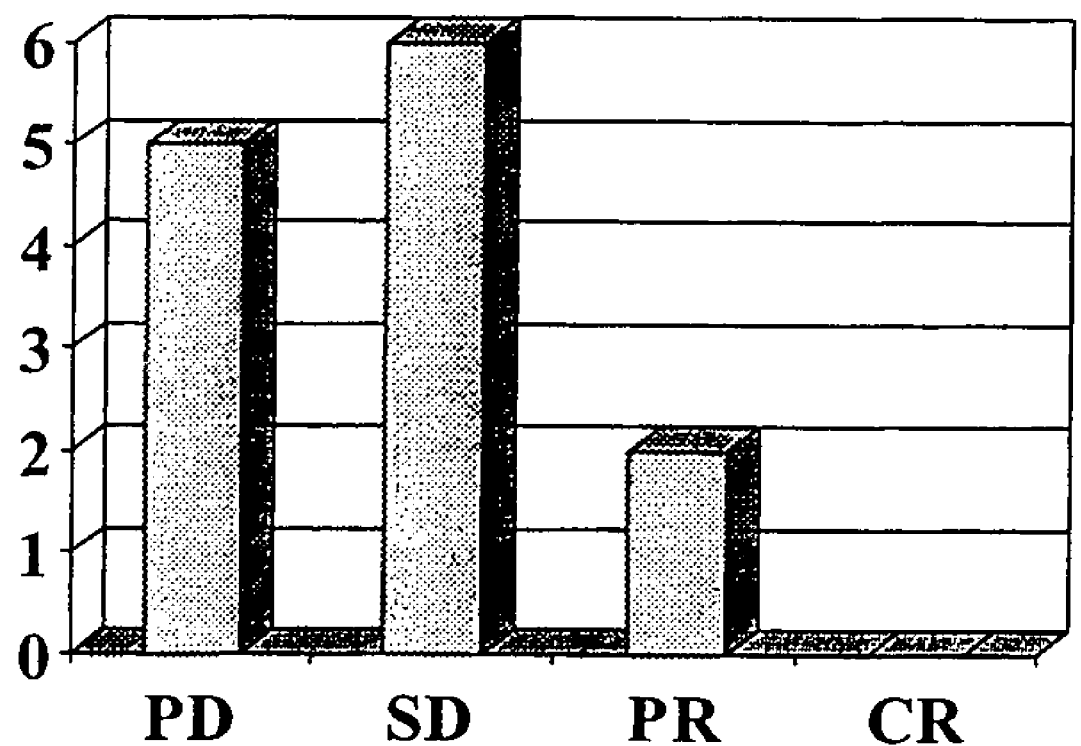
FIG. 3. Histogram showing the response evaluation of patients with metastatic breast cancer who were treated with r-hCG. The patients were categorized as follows: PD=progressive Disease; SD=Stable Disease; PR=Partial Response; CR=Complete Response.

The content of PgR was also considered to be positive when more than 20% of tumoral cells were positive for this antibody. In six of the cases in which the initial NB was positive it became PgR negative after treatment. In those cases in which the initial biopsy was negative the post-treatment excisional biopsy was also negative. In five of the cases in which the NB was positive the lymph node metastases were negative for PgR. Placebo treated patients did not exhibit changes in the PgR status of their tumors. FIGS. 2 and 3 depict the values ER and PR positive cells, respectively, expressed as a percentage.

Immunostaining for inhibin. In nine out of the eighteen primary breast cancer patients that received r-hCG a significant increase in immunoreactivity was observed in the neoplastic cells. This effect was not observed in the tissue samples of patients that received the placebo.

Hormonal profile. The levels of the six hormones were measured in the serum of breast cancer patients receiving r-hCG or placebo. There was a significant difference in the levels of b-hCG detected in the serum of the patients treated with r-hCG over those receiving the placebo at 5, 9 and 13 days of treatment ($p<0.0001$, $P<0.004$ and $p<0.007$, respectively). There was no statistically significant increase in the level of LH in the r-hCG over the placebo treated patients at any of the time points sampled. Neither the r-hCG nor the placebo treatments modified the levels of FSH, estradiol, inhibin, and progesterone.

Conclusions

In the present work we have demonstrated that a 2-week treatment with r-hCG administered as described above to postmenopausal women with newly diagnosed primary breast cancer induces a marked and significant reduction in cell proliferation in the primary tumor. An interesting observation was that the lymph nodes of the same patients exhibited in the metastatic cells a level of cell proliferation similar to that of the post-r-hCG treatment tumors, but no changes were observed in placebo treated women.

Recombinant hCG treatment induced down-regulation of ER and PgR expression in six out of nine and six out of ten positive cases, respectively. R-hCG did not modify the serum levels of estradiol, progesterone, inhibin, FSH or LH, and the values detected were those reported for menopausal women. R-hCG neither produced clinical side effects in the patients or alterations in their hormonal milieu. These observations are the first indication that r-hCG has an antiproliferative effect in primary and metastatic breast cancers without inducing alterations in the overall well being of the patient. The data reported in this work indicate that hCG has a direct effect on neoplastic cells and that the ovarian hormones do not mediate this effect. Our patients are postmenopausal women in which the hormonal milieu clearly shows that it was not affected after the r-hCG administration.

The local production of inhibin by the neoplastic cells was overexpressed in 50% of the primary breast lesions of patients treated with r-hCG. Due to the limitations of the quantitation by pluses, we have only reported those cases in which significance differences were observed. Western blot analysis would be desirable for a quantitative evaluation of this marker.

At systemic level, the only hormone that was elevated by the r-hCG treatment was b-hCG. The correlation between the decrease in cell proliferation and the increase in b-hCG level was striking.

EXAMPLE 2

Recombinant Human Chorionic Gonadotrophin Inhibits Metastatic Breast Cancer in Postmenopausal Women An open-label, single center study was conducted to test the inhibitory effect of recombinant human chorionic gonadotropin (r-hCG) on metastatic breast cancer in postmenopausal women. The primary objective of this study was to assess the effect of r-hCG on the tumor response rate of bi-dimensionally measurable or palpable lesions. The secondary objectives were: i.) to assess the effect of r-hCG treatment on symptoms caused by metastatic breast tumor lesions, ii.) to determine whether r-hCG exerts any adverse systemic effects, iii.) to measure time to tumor progression and, iv.) to determine the effects of r-hCG on endocrinology parameters and tumor markers.

Thirteen postmenopausal women diagnosed with biopsy-proven breast cancer and clinical evidence of metastatic disease were entered in the study. Patients are treated with 500 mcg of r-hCG three times per week for at least two months. Tumor assessment and measurement of target indicator lesions are performed every two months by X-ray, CT scan, MRI or physical examination. After 60 days of treatment, a re-evaluation of metastatic lesions is performed using the same diagnostic procedure(s). In the event of disease progression (i.e., appearance of new tumor or growth of indicator lesions by at least 25% in square dimensions) study treatment is discontinued, otherwise, treatment is continued, with patient re-evaluations every eight weeks, until progressive disease is noted.

One patient died due to complications of breast cancer prior to the 60 day visit, twelve patients completed the 60 day visit. Of these 12, four patients dropped out due to progressive disease and eight patients remain on active treatment in the maintenance phase of the study (FIG. 3). Two patients have been classified as partial responses, on the basis of greater than 50% reduction in liver metastases. Six of the thirteen patients had stable disease.

These first clinical data show that hCG is effective in the treatment of metastatic mammary tumors in postmenopausal women.

EXAMPLE 3

Human Chorionic Gonadotrophin Protects Against Tumor Initiation and Inhibits Tumor Growth in Rats at Early and Late Stages of Tumor Development Having clinically demonstrated the efficacy of hCG in the treatment of primary and metastatic mammary tumors in post-menopausal women, the inventors sought to extend and clarify their observations through the use of an established animal model system. The experimental results set forth in this example demonstrate in the rat model system that urinary or recombinant human chorionic gonadotropin (u-hCG or r-hCG) have a protective effect against development of breast cancer, and a therapeutic effect against early and late stage mammary tumors.

Experimental Protocol and Procedures

Evaluation of the efficacy of r-hCG in the prevention of mammary cancer: Regimens 1–9 utilized in the experiments described below are shown schematically in FIG. 4. The animals utilized in Regimens 1–9 consisted of 450 intact virgin Sprague-Dawley rats that were purchased from Taconic Farms (New York, N.Y.).

The potential of hCG to inhibit the initiation of DMBA-induced rat mammary carcinomas was evaluated in intact virgin rats treated with placebo (Regimen 1); 100 IU r-hCG/day (Regimen 2), or 100 IU u-hCG/day (Regimen 3). All animals were injected daily for 21 days, starting when the rats were 45 days old. The carcinogen DMBA was administered as a single intragastric dose (8 mg/100 g body weight) given 21 days after the last injection of placebo or hormone. Under these protocols the first effect evaluated was the appearance of tumors detected by palpation and their location with regards to specific mammary glands. Other parameters evaluated were the rate of tumor growth, tumor ulceration, and tumor regression or ulcer healing and tumor necrosis in response to the hormonal treatment. These results were correlated with the baseline level of differentiation of the mammary parenchyma, rate of cell proliferation, level of expression of genes controlling programmed cell death, rate of apoptosis and inhibin synthesis in the mammary epithelium at the time of carcinogen administration.

Figure 4:
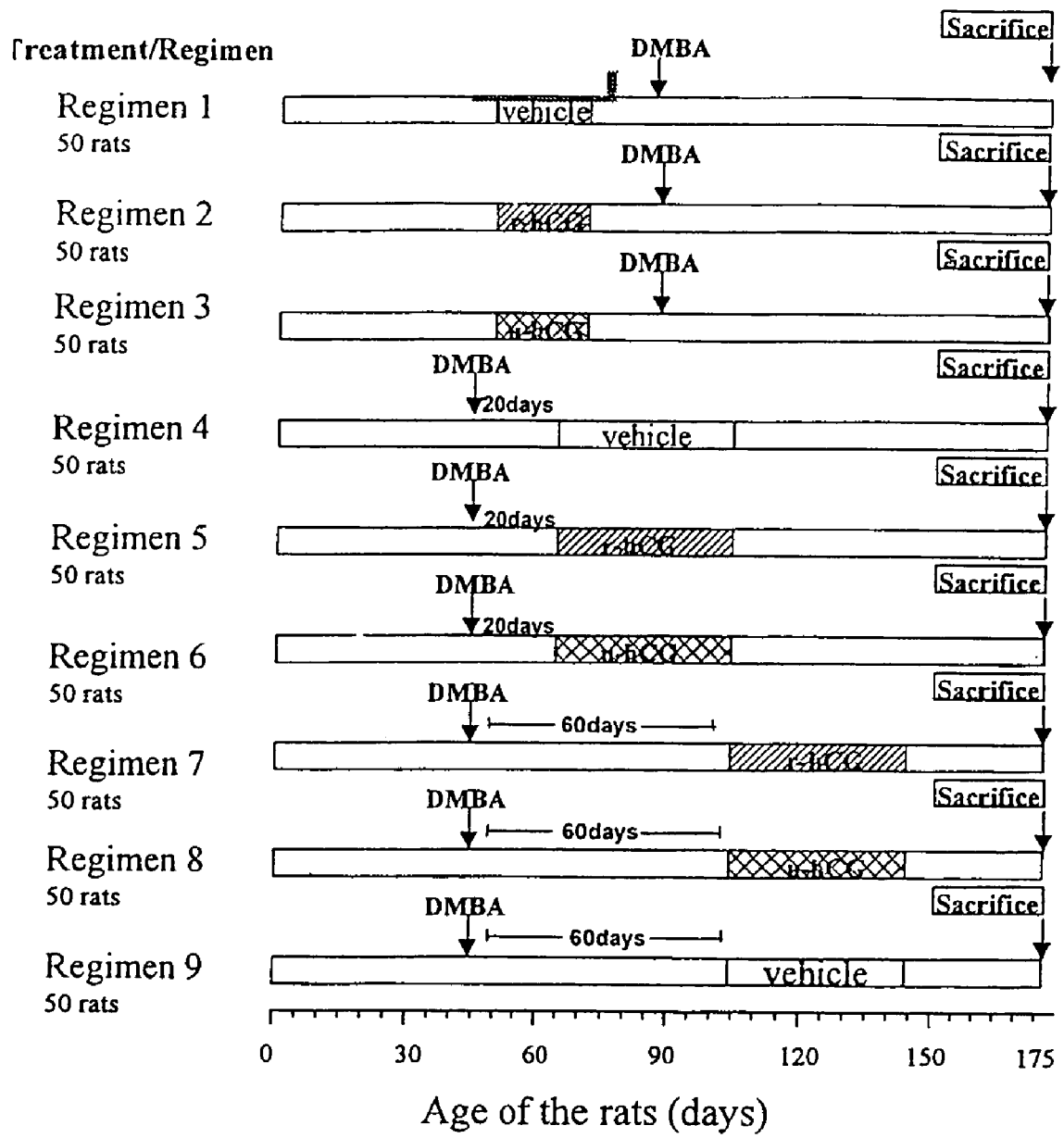
FIG. 4. Schematic diagram of experimental protocol designed for testing the preventive and therapeutic efficacy of recombinant and urinary human chorionic gonadotropin (hCG) on rat mammary cancer in vivo.

Evaluation of the therapeutic efficiency of r-hCG on mammary cancer. The tumoristatic and tumoricidal efficacy of r-hCG and u-hCG on early and advanced mammary cancer was tested in intact virgin rats that had received a single dose of DMBA when they were 45 days old (FIG. 4, Regimens 4–9). The effect on early tumor development was tested under Regimens 4, 5, and 6. It was evaluated by initiating r-hCG treatment 20 days after DMBA administration, when early lesions, such as intraductal proliferations (IDPs) and carcinomas in situ (CIS) are already present, but there are no palpable tumors as yet. The effect on advanced tumor development was evaluated by starting the hormonal treatment 60 days after DMBA administration, or when palpable tumors had reached at least 1 cm in maximal diameter (Regimens 7, 8, and 9). In both groups the hormone was administered for 40 days and final tumorigenic response was evaluated 20 weeks post-DMBA administration. The effect of the hormonal treatment on the rate of tumor growth, with special emphasis on tumor regression, absence of skin ulceration, and final tumor size and necrosis were evaluated at the time of assessment of the final tumorigenic response. These results were correlated with the rate of cell proliferation, expression of inhibin synthesis, estrogen and progestin receptor content, expression of programmed cell death genes and of apoptosis in tumors developed by r-hCG and u-hCG treated animals in comparison with those developed by rats that received the placebo.

All treatments were initiated when the animals were 45 days old. For Regimen 1 fifty rats received a daily intraperitoneal (ip) injection of 0.5 ml placebo for 21 days. Under Regimens 2 and 3 the same number of animals received for 21 days 100 IU/day of r-hCG or u-hCG (Steris Laboratories, Phoenix, Ariz.) respectively. Twenty-one days after completion of the last injection, when the animals were 87 days old, the three groups of animals were inoculated with a single intragastric (ig) dose of 8 mg DMBA (Sigma Chemical Co., St. Louis, Mo.) per 100 g body weight (bw). Thereafter all the animals were palpated periodically for detection of tumor development and determination of tumor growth rate. Final tumorigenic response was evaluated 15 weeks after administration of DMBA.

For Regimens 4–9, 300 animals were inoculated with a single ig dose of 8 mg DMBA/100 g bw when they were 45 days old. Tumorigenic response was evaluated by palpation of the right and left mammary cervical, thoracic, abdominal and inguinal areas and from ventral to dorsolateral extensions of the glands. All tumors were sequentially numbered in the order they had appeared, their location was recorded, and the rate of tumor growth was determined by measurement of tumor size with a Vernier caliper. All changes in the health status of the animals, rapid tumor growth or skin ulceration were recorded. Those animals in which the tumors were excessively large or became ulcerated were euthanized, irrespectively of the stage of the hormonal treatment, in compliance with IACUC regulations. Those animals that were euthanized before initiation or before the completion of the hormonal treatments were deleted from the statistical analysis of the final tumorigenic response.

Regimens 4–6 were designed for testing the effect of the hormonal treatments on early tumor development. Twenty one days after DMBA administration those animals allocated to Regimen 4 started receiving a daily ip injection of 0.5 ml placebo for 40 days. Under Regimens 5 and 6 the same number of animals received for 40 days 100 IU/day of r-hCG or u-hCG, respectively. All the animals were palpated biweekly for detection of tumor development and determination of tumor growth rate. Final tumorigenic response was evaluated 20 weeks after administration of DMBA.

Regimens 7–9 tested the effects of r-hCG and u-hCG on late (palpable) tumor development: Sixty days after DMBA inoculation, when the rats were 105 days old, animals allocated to Regimen 7 started receiving a daily ip injection of 100 IU/day r-hCG for 40 days. Under Regimens 8 and 9 the same number of animals received for 40 days 100 IU/day of u-hCG or 0.5 ml placebo, respectively. Tumorigenic response was evaluated by biweekly palpation. All tumors were sequentially numbered, their location was recorded, and the rate of tumor growth was determined by measurement of tumor size with a Vernier caliper. Final tumorigenic response was evaluated 20 weeks after administration of DMBA.

Evaluation of Final Tumorigenic Response. At the end of the experiment all the animals were anesthetized with an ip injection of Ketamine (90 mg/Kg bw)-Nembutal (40 mg/Kg bw), bled through the inferior vena cava, and the serum was separated and kept frozen at −70° C. The tumors were rapidly dissected, measured in three dimensions, and serially sliced. Adjacent slices were:

1) fixed in 10% neutral buffered formalin (NBF) for histopathological and immunocytochemical analysis, 2) frozen in liquid nitrogen for RNA extraction, 3) frozen in liquid nitrogen for estrogen receptor (ER)-progesterone receptor (PR) determinations, and 4) placed in sterile culture medium for DNA analysis by flow cytometry.

Tumors that were smaller than 1 cm in diameter were fixed in 10% NBF only. In the absence of tumors the right thoracic ($2^{nd}$ and $3^{rd}$), and the right abdominal ($4^{th}$) mammary glands were fixed in 10% NBF for histopathological evaluation of degree of gland development. The right and left ovaries of all animals were dissected, measured in three dimensions with a Vernier caliper and fixed in 10% NBF. All the internal organs were examined for evidence of metastatic nodules, adhesions, or hemorrhages. Liver, spleen, and lung changes were documented and representative fragments of tissues were fixed in 10% NBF for histopathological examination. Representative lesions were photographed.

The following criteria were utilized for evaluating the final tumorigenic response:

1. Rate of tumor growth, based on sequential measurement of the two largest diameters of tumors in live animals utilizing a Vernier Caliper and expressing the results in mm.

2. Final tumor size, based on measurement of the length, width and height of dissected tumors with a Vernier Caliper. Results were expressed in mm. A progressively smaller tumor size in successive measurements was indicative of tumor regression. Palpable tumors that had disappeared at the time of dissection were considered to be 100% regressed. The mammary tissue in which the tumor had been originally identified was fixed in 10% NBF for histopathological analysis. This criterion was indicative of an inhibitory effect of the hormonal treatments on tumor growth.

3. Tumor necrosis in large palpable tumors. Even though in hormonally treated animals the mammary tumors retained their original size or continued growing, upon dissection the tumors were observed to consist of a soft cystic formation filled with necrotic tissue in which there was almost no viable tissue. These signs were interpreted to be indicative of tumor destruction induced by the hormonal treatment, and equivalent to tumor regression induced by the hCG treatment.

4. Presence of skin ulceration in live animals, indicative of rapid rate of tumor growth, more frequently found in placebo treated animals. This condition made it mandatory to euthanize the animals.

5. Statistical Analysis. The significance of the differences in tumorigenic response among the groups was determined by Chi Square analysis and Student's T test.

Results

Effect of r-hCG and u-hCG in the prevention of mammary cancer-Regimens 1, 2, and 3. Virgin rats treated with placebo, r-hCG or u-hCG for 21 days, and that received DMBA 21 days after the last injection when they were 87 days old, appeared healthy throughout the length of the study. One animal of Regimen 1 and one of Regimen 2 died as a consequence of acute reaction to the anesthesia and were deleted from the study, reducing the total animal population to 49 in each one of these two regimens. None of the animals required to be euthanized before the end of the experiment. The vast majority of tumors were found at the time of autopsy and none of them were ulcerated.

Figure 5:
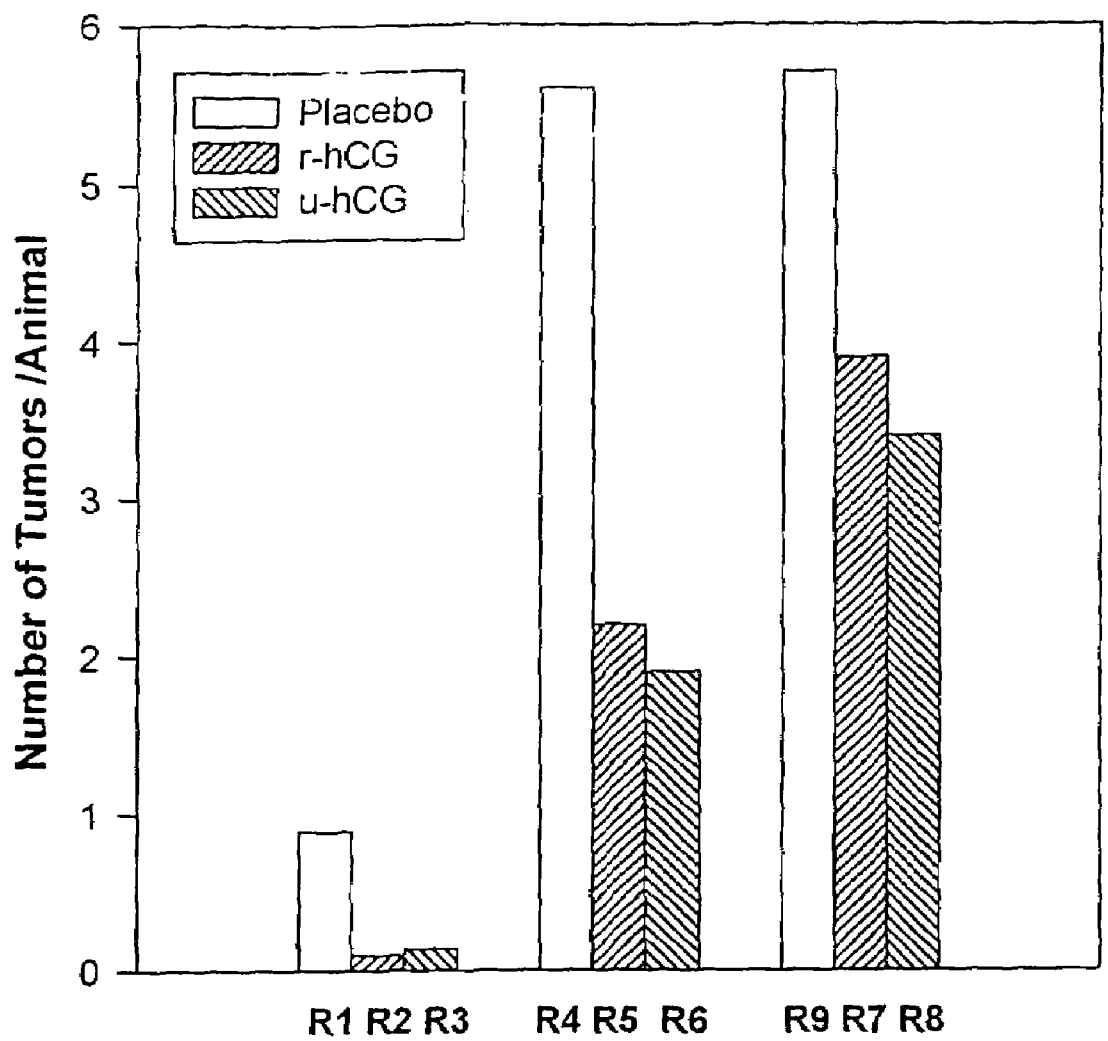
FIG. 5. Effect of Placebo, r-hCG and u-hCG on tumor burden. Number of tumors per animal in virgin rats treated with placebo, Regimens 1 (R1), 4 (R4), and 9 (R9); recombinant hCG, Regimens 2 (R2), 5 (R5), and 7 (R7), or urinary hCG, Regimens 3 (R3), 6 (R6), and 8 (R8) at the times indicated in FIG. 4.

Treatment of the animals with hCG significantly reduced the number of tumors in all the mammary glands and no tumors were found in the neck and ear region (ear duct tumors); the number of animals with tumors was reduced from 22/49 (22 of 49 total animals) to 4/49 or 6/50, respectively, for r-hCG and u-hCG. As shown in FIG. 5, the number of tumors per animal was also significantly decreased, from 0.89 (placebo) to 0.10 (r-hCG) and 0.14 (u-hCG), respectively.

Effect of r-hCG on early tumor development. Regimens 4, 5, and 6. From the 50 animals inoculated with DMBA one animal from Regimen 4 and one from Regimen 5 died due to acute reaction to the anesthesia. The treatment of the remaining animals with placebo, r-hCG, or u-hCG was initiated 21 days after administration of the carcinogen (FIG. 4).

Ten of the 49 animals of Regimen 4 (placebo) had developed at least one palpable tumor by 42 days post-DMBA administration. One animal that was severely ill and died at the time of the fourteenth placebo injection was deleted from the final analysis. Two animals that died 12 and 14 days after the last injection were included in the final analysis. One of these was free of tumors and the other had three palpable tumors.

As observed in the preventative regimens, treatment of the animals with hCG significantly reduced the number of tumors in mammary glands and non-mammary tissue; the number of animals with tumors was reduced from 48/49 to 38/49 or 30/46, respectively, for r-hCG and u-hCG. As shown in FIG. 5, the number of tumors per animal was also significantly decreased, from 5.6 (placebo) to 2.2 (r-hCG) and 1.9 (u-hCG), respectively.

Effect of r-hCG on advanced tumor development. Regimens 7, 8, and 9. From the 50 animals inoculated with DMBA one animal from Regimen 7 died during carcinogen administration and was deleted from the study. From the final analysis of tumorigenic response were also deleted all those animals that needed to euthanized because of the rapid growth and ulceration of the tumors before completion of treatment. The same criteria applied to the animals treated with r-hCG (Regimen 7), u-hCG (Regimen 8), and placebo (Regimen 9).

In the placebo treated animals (Regimen 9) a total of 40 animals were euthanized after completion of treatment and adequate follow up. Thirty nine of them had a total of 229 tumors, with an average of 5.7 tumors per animal, in a distribution similar to that observed for regimens 1–6. In addition two animals had metastatic nodules in the spleen, liver, and lung, which were not included in the final tabulation of tumors.

In the r-hCG treated group (Regimen 7), a total of 37 animals fulfilled the eligibility criteria to be included in the final analysis; 33 of them developed a total of 147 tumors, averaging 4.4 tumors per animal with tumors, or 3.9 tumors per total number of animals at risk. Thirty two out of the 36 animals treated with u-hCG (Regimen 8) developed tumors, with an average of 3.4 tumors per animal.

Figure 6:
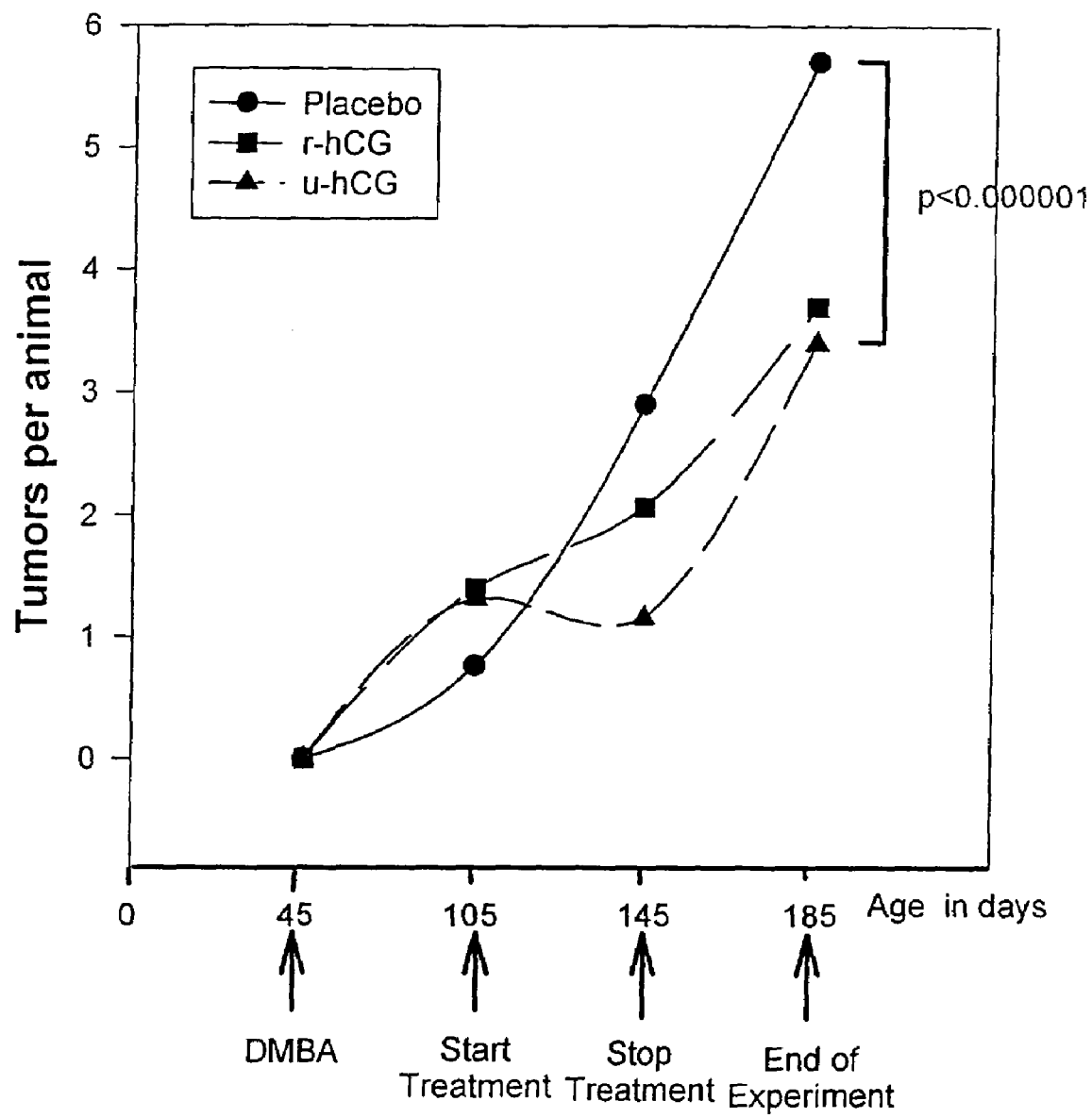
FIG. 6. Graph showing time-course of inhibition of tumor burden in rats by r-hCG and u-hCG.

Results of regimens 1–9 are summarized in Table 1 below, and are shown in FIGS. 5 and 6.

TABLE 1

Summary of Tumorigenic Response in Animals
Treated with placebo, Regimens 1, 4, and 9; r-hCG,
Regimens 2 5 and 7, or u-hCG, Regimens 3, 6, and 8.

| Regimen | No. Animals | No. An. With Tumors | Percentage[1] | Total No. Tumors | No. Tumors/ Animal |
|---|---|---|---|---|---|
| 1 | 49 | 22 | 44.9 | 44 | 0.89 |
| 2 | 49 | 4 | 8.1 | 5 | 0.10 |
| 3 | 50 | 6 | 12.0 | 7 | 0.14 |
| 4 | 49 | 48 | 97.9 | 273 | 5.6 |
| 5 | 49 | 38 | 77.5 | 111 | 2.2 |
| 6 | 46 | 30 | 65.2 | 88 | 1.9 |
| 9 | 40 | 39 | 97.5 | 229 | 5.7 |
| 7 | 37 | 33 | 89.1 | 147 | 3.9 |
| 8 | 36 | 32 | 88.8 | 122 | 3.4 |

[1]Significant differences in tumor incidence analyzed by Chi square were: Regimen 1 versus Regimen 2 = 16.96, $p < 0.00003$; Regimen 1 versus Regimen 3 = 13.20, $p < 0.0002$; Regimen 4 versus Regimen 5 = 9.49, $p < 0018$; Regimen 4 versus Regimen 6 = 17.3, $p < 0.00003$. The differences between r-hCG Regimens 2, 5, and 7, versus u-hCG, Regimens 3, 6, and 8, and between Regimens 9, 7, and 8 were not significant.

Conclusions

The results set forth above indicate that administration of urinary or recombinant hCG to young virgin rats prevents the initiation and inhibits the progression of DMBA-induced tumors. A 21 day treatment with r-hCG produces a preventive effect, even when the treatment had been terminated 21 days prior to carcinogen administration. Similar results were obtained with u-hCG.

The results also revealed that r-hCG treatment of rats previously inoculated with DMBA inhibited the development of early mammary lesions, since initiation of the hormonal treatment 20 days after carcinogen administration reduced significantly both tumor incidence and tumor burden. Both r-hCG and u-hCG exhibited similar tumor inhibitory effects. These data have a significant clinical implication, because they indicate the usefulness of the utilization of this hormonal treatment on early as well as on premalignant lesions. These results show that the sooner a treatment is started, the more efficient is the therapeutic effect of these hormones.

When the hormonal treatments were initiated 60 days after administration of DMBA, tumor burden, expressed as the number of tumors per animal, were also significantly depressed. FIG. 6 clearly shows that both r-hCG and u-hCG reduce significantly the tumor burden and reduce the growth of tumors, as evidenced by the lower number of tumors per animal after cessation of the hormonal treatments. The analysis of the final tumorigenic response demonstrated that the placebo treated animals had 40% more tumors than those treated with either hormone (FIG. 5). It is important to analyze the slope of the curve between the initiation (start) and finalization (stop) of the treatment shown in FIG. 6. Both hormones induce a decline in the slope of the curve due to the direct effect of the hormones on tumorigenesis. At the end of treatment the slope of the curve became steeper, but it never reached that of the animals that had received the placebo, an indication that both hormones have an efficient therapeutic effect by reducing tumor burden by 40%. These results suggest that r-hCG would be more efficient as a therapeutic tool when used in not only one but probably multiple cycles of treatment in order to be fully curative.

EXAMPLE 4

Inhibition of Breast Cancer Cells by hCG and Tamoxifen In Vitro

Preliminary in vitro experiments were carried out on CG-5 cells, a variant of the MCF-7 cell line (Natoli C. et al., 1983, Breast Cancer Res. Treat. 3:23–32) characterized by a high degree of estrogen responsiveness and an appreciable content of estrogen, androgen, glucocorticoid and progesterone receptors.

Experimental Protocol and Procedures

Cells were routinely cultured in Dulbecco's modified Eagle's medium (DMEM) supplemented with 10% fetal calf serum (FCS) and antibiotics. For cell growth experiments, cells were plated out at the density of 50,000 cells/ml in the medium described above. Twenty-four hours later, the medium was replaced with fresh medium containing 5% charcoal-treated FCS(CH-FCS) plus a fixed concentration ($10^{-7}$ M) of Tamoxifen (TAM) and various concentrations (from 10 to 10,000 IU/ml) of hCG. Medium was renewed every 3 days. In the experiments concerning the effect of hCG and TAM sequentially added to CG-5 cells, cells were plated out at 50,000 cells/ml, as described above, and 24 hours later DMEM was changed with fresh medium containing 10 to 10,000 IU/ml of hCG. For each concentration of hCG, a different number of plates were prepared in order to have a sufficient number of cells to be replaced at the end of the treatment (as hCG has an inhibitory effect itself). After 1 week of exposure to hCG, CG-5 cells were plated in medium supplemented which 10% FCS and antibiotics, and 24 hours later DMEM was replaced by fresh medium supplemented with 5% CE-FCS and a fixed concentration of TAM ($10^{-7}$ M). Medium was renewed every 3 days. In all experiments performed cells were counted, after 3 to 6 days, with the use of an hemocytometer.

Results

The simultaneous addition to CG-5 cultures of a fixed concentration of TAM ($10^{-7}$ M) combined with concentrations ranging from 10 to 1,000 IU/ml of hCG, produces an inhibition of cell proliferation which is not related to the dose of hCG but is higher than that induced by TAM alone. At the lowest concentration of hCG, the inhibition of cell proliferation was about 50% with respect to control on the third day from the addition of the two drugs to the culture medium. When cells are treated for 6 days with the combination TAM-hCG, the inhibition of cell proliferation becomes dependent on the dose of hCG and reaches 65% with respect to controls at 1,000 IU/ml of the drug.

CG-5 cells were also pretreated with different concentrations of hCG and subsequently exposed to $10^{-7}$ M TAM. On the third day after the addition of the antiestrogen to the culture medium, an inhibition of approximately 50% of cell proliferation with respect to control is found in the cells which have received the highest concentration of hCG. On the sixth day after the addition of TAM to the culture medium, the most pronounced inhibition of cell proliferation is obtained in CG-S cells pretreated with the lowest concentration of hCG (about 65% with respect to control) and it remains unmodified in cells pretreated with increasing doses of the drug.

Figure 7A:
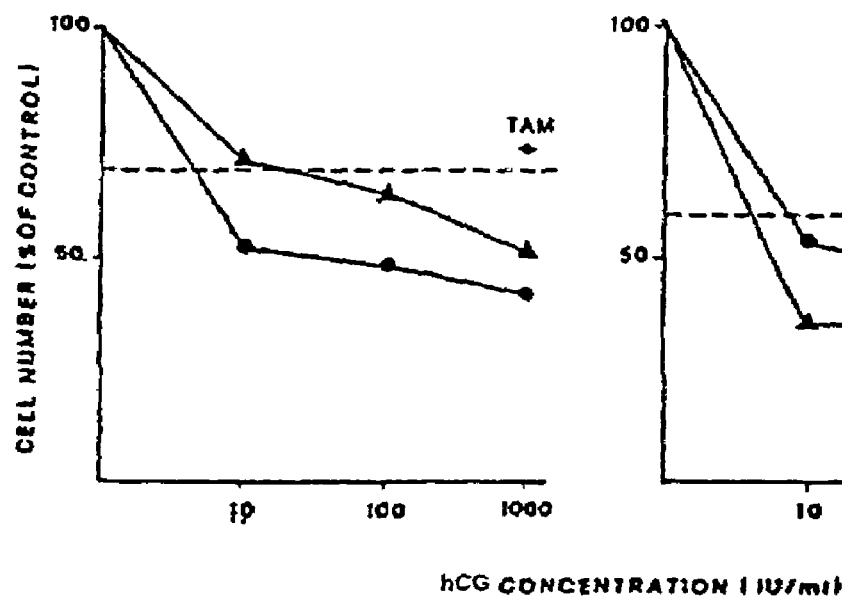
FIG. 7. Proliferation experiments using the human breast cancer cell line CG-5. The cells were grown in a culture medium containing a fixed amount of Tamoxifen (TAM) and various concentrations of hCG. Cells were counted after 3 days (FIG. 7A) and 6 days (FIG. 7B) and cell counts are expressed as the percent of the number of control cells. Dotted line represents the effect of $10^{-7}$ M tamoxifen alone. The tamoxifen is added either simultaneously with (solid circles or sequentially to (solid triangles) the hCG.
Figure 7B:
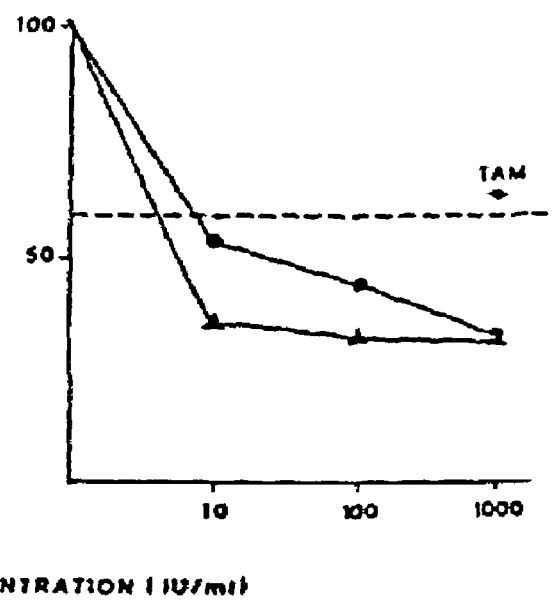

Results are summarized in FIGS. 7a and 7b, which illustrate graphically the comparison between the different modalities (combined or sequential treatment) used to study the effect of Tamoxifen and hCG on cell growth. Graphs a and b demonstrate the effect of hCG and Tamoxifen added simultaneously (large dot symbol) or sequentially (triangular symbol) to CG-5 cells on the third (a) and sixth (b) day from the addition of the compounds to the culture medium. In the case of sequential administration, cells were pretreated with the hCG concentration indicated in the figure and then exposed to Tamoxifen. The dotted line ( - - - ) represents the effect of $10^{-7}$ M Tamoxifen alone, evaluated in parallel experiments not reported in the text.

Figure 8:
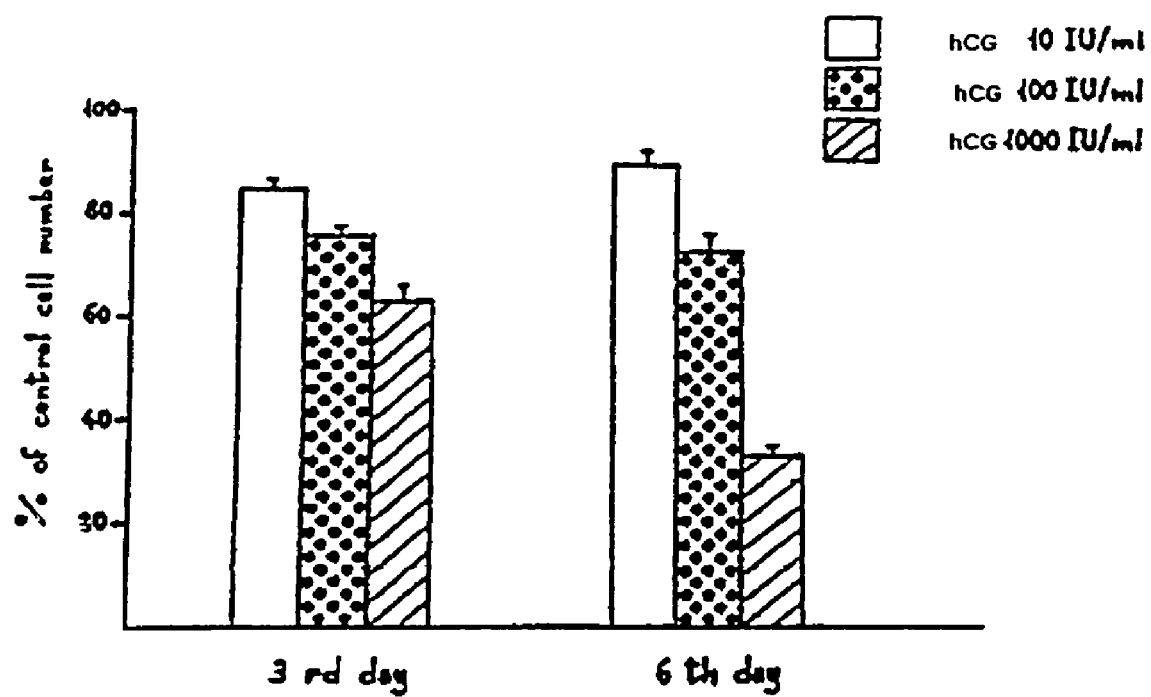
FIG. 8. Histogram showing results of proliferation experiment using the human breast cancer cell line CG-5, wherein the culture medium was supplemented with hCG alone.

FIG. 8 shows the effect of hCG alone on the growth of CG-5 cells cultured in identical experimental conditions. In this case the inhibition of cell proliferation is evident after three days of exposure to the hCG starting from the concentration of 100 IU/ml. After six days of treatment with hCG, the inhibitory effect on cell proliferation significantly increases only at the maximum dose of 1000 IU/ml.

The comparison between FIGS. 7 and 8 clearly shows that such low doses of hCG as 10 IU/ml are efficacious when combined with the anti-estrogen, whereas the same doses are practically ineffective if hCG is used alone. Similar conclusions are reached if the effect of Tamoxifen alone is compared with the combined effect of Tamoxifen with hCG.

The present invention is not limited to the embodiments described and exemplified above, but is capable of variation and modification without departure from the scope of the appended claims.

We claim:

1. A method of treating metastatic mammary tumors in postmenopausal women, comprising the steps of:
    a) detecting a metastatic mammary tumor in a postmenopausal woman;
    b) administering to the postmenopausal woman a first dose of hCG; and
    c) administering to the postmenopausal woman one or more subsequent doses of hCG, wherein the first dose and the subsequent doses of hCG are administered in an amount and over a period of time effective to inhibit proliferation of mammary tumor cells, thereby treating the metastatic mammary tumors.

2. The method of claim 1, combined with at least one other treatment for metastatic mammary tumors.

3. The method of claim 2, wherein the at least one other treatment is surgery or chemotherapy.

4. The method of claim 1, wherein the mammary tumors comprise cells that are estrogen receptor-positive.

5. The method of claim 1, wherein the hCG is administered in an amount of 100 to 20,000 IU per day.

6. The method of claim 1, wherein the hCG is administered in amount of 50 to 50,000 micrograms per day.

7. The method of claim 6, wherein the hCG is administered in an amount of 250 to 3,000 micrograms per day.

8. The method of claim 1, wherein the one or more subsequent doses of hCG are administered every second day following administration of the first dose.

9. The method of claim 1, wherein the one or more subsequent doses of hCG are administered three times each week following administration of the first dose.

10. The method of claim 1, wherein the one or more subsequent doses of hCG are administered for several weeks following administration of the first dose.

11. The method of claim 10, wherein the hCG is administered for at least 12 weeks.

12. The method of claim 1, wherein the hCG is administered subcutaneously.

13. The method of claim 1, wherein the hCG is administered in combination with Type 1 interferon.

14. The method of claim 1, wherein the hCG is recombinant hCG.

* * * * *